United States Patent [19]

Kronberg

[11] Patent Number: 5,316,649
[45] Date of Patent: May 31, 1994

[54] HIGH FREQUENCY REFERENCE ELECTRODE

[75] Inventor: James W. Kronberg, Aiken, S.C.

[73] Assignee: The United States of America as represented by the United States Department of Energy, Washington, D.C.

[21] Appl. No.: 665,640

[22] Filed: Mar. 5, 1991

[51] Int. Cl.$^5$ ..................... G01N 27/30; G01N 27/32
[52] U.S. Cl. ..................... 204/435; 204/400
[58] Field of Search ..................... 204/435, 402, 400

[56] References Cited

U.S. PATENT DOCUMENTS

| | | | |
|---|---|---|---|
| 1,865,004 | 6/1932 | Haring | 204/435 |
| 2,563,062 | 8/1951 | Perley | 204/435 |
| 2,685,673 | 8/1954 | Avins | 324/72.5 |
| 2,755,243 | 7/1956 | Beckman et al. | 204/435 |
| 2,883,619 | 4/1959 | Kobbe et al. | 324/72.5 |
| 3,505,195 | 4/1970 | Nielsen et al. | 204/435 |
| 3,756,936 | 9/1973 | Neuwelt | 204/435 |
| 3,855,095 | 12/1974 | Leonard et al. | 204/435 |
| 3,880,737 | 4/1975 | Brunt | 204/435 |
| 3,959,107 | 5/1976 | Horner et al. | 204/435 |
| 4,217,194 | 8/1980 | Lubbers et al. | 204/435 |
| 4,255,244 | 3/1981 | Matsuyama et al. | 204/435 |
| 4,360,415 | 11/1982 | Brezinski | 204/435 |
| 4,418,314 | 11/1983 | Nieto, Jr. | 324/72.5 |
| 4,480,223 | 10/1984 | Aigo | 324/158 |
| 4,646,005 | 2/1987 | Ryan | 324/123 |
| 4,778,063 | 10/1988 | Ueberreiter | 209/573 |

OTHER PUBLICATIONS

Mansfield et al., *J. Electrochemical Soc.*, vol. 135, pp. 906–907, Apr., 1988.

*Primary Examiner*—T. Tung
*Attorney, Agent, or Firm*—Brian R. Tumm; Harold H. Dixon; William R. Moser

[57] ABSTRACT

A high frequency reference electrode for electrochemical experiments comprises a mercury-calomel or silver-silver chloride reference electrode with a layer of platinum around it and a layer of a chemically and electrically resistant material such as TEFLON around the platinum covering all but a small ring or "halo" at the tip of the reference electrode, adjacent to the active portion of the reference electrode. The voltage output of the platinum layer, which serves as a redox electrode, and that of the reference electrode are coupled by a capacitor or a set of capacitors and the coupled output transmitted to a standard laboratory potentiostat. The platinum may be applied by thermal decomposition to the surface of the reference electrode. The electrode provides superior high-frequency response over conventional electrodes.

12 Claims, 2 Drawing Sheets

HIGH FREQUENCY REFERENCE ELECTRODE

The United States Government has rights in this invention pursuant to Contract No. DE-AC09-89SR18035 between the U.S. Department of Energy and Westinghouse Savannah River Company.

BACKGROUND OF THE INVENTION

1. Field of the Invention

The present invention relates to electrodes for electrochemical experiments. In particular, the present invention relates to reference electrodes that provide a high frequency response.

2. Discussion of Background

An electrochemical reference electrode, or "half-cell", typically uses the reversible conversion of either mercury or silver to the corresponding, sparingly water-soluble chloride to establish a current path between an aqueous solution and external circuitry. For example, a calomel electrode consists of a small amount of mercury surrounded by calomel ($Hg_2Cl_2$) and potassium chloride (KCl) solution held in a glass tube. Electrical contact is made to the mercury via a platinum wire extending through the glass tube, and between the KCl solution in the tube and an external fluid through a porous plug that allows ion diffusion but no bulk flow. Small electric currents flowing between the platinum wire and the external fluid either reduce some of the calomel to metallic mercury or oxidize some of the mercury to calomel according to the following reaction:

$$Hg_2Cl_2 + 2e^- \rightleftharpoons 2Hg + 2Cl^-$$

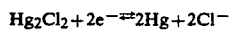

Since the mercury-calomel (or silver-silver chloride) half-cell potentials are precisely known, and these electrodes therefore provide a "reference" potential, the potential developed by any other type of electrode (or sample) placed in the external fluid, which electrode is part of the other half-cell, can be found easily by subtracting the reference potential from the total. However, currents must be kept small if the potential is not to be obscured by solution resistance and quasi-resistive effects caused by finite ion diffusion speeds. Consequently, the impedance of a calomel electrode may range from a hundred ohms to several thousand ohms, depending on its construction and history of use.

Calomel and silver-chloride electrodes are classically used in measuring steady-state, D.C. voltages. However, in some research areas—for instance, in the study of corrosion films—additional data can be gathered by introducing a small amount of high-frequency A.C. and monitoring it along with the usual D.C. signal. Unfortunately, conventional laboratory amplifiers (potentiostats) generally have significant input capacitance which can shunt much of the high-frequency signal to ground, thus obscuring the high-frequency phenomena of interest.

Another type of electrode widely used in studying chemical systems is a bare platinum rod, wire or plate, directly immersed in the liquid under study. Such an electrode generates a voltage which varies with the relative concentrations of reduced and oxidized ions in the liquid; this is sometimes called the "redox" potential. Unlike the calomel and silver-chloride electrodes used for reference potential measurements, a platinum electrode has a very low impedance, since current flows easily between the bare metal of the electrode and the liquid in which it is immersed.

A method of overcoming the high-frequency limitations of standard reference electrodes was described by Mansfield, Lin, Chen, and Shih (*J. Electrochem. Soc.* 135, 906), in which the reference electrode is mounted side-by-side with a small platinum electrode and the two are coupled together by a capacitor. By blocking D.C. signals, the capacitor prevents the reference potential from being swamped by the much stronger (because of lower impedance) redox potential. At high frequencies, however, the capacitor allows extra signal power from the platinum electrode to flow over into the reference electrode circuit and hence to the potentiostat, largely overcoming the high-frequency losses present in the conventional reference electrodes.

While electrically favorable, the design of Mansfield, et al. still has disadvantages. If the distance between the two parts of the electrode is significant on the scale of the test apparatus, many factors can come into play to distort the test results. For example, if an A.C. signal flows in a direction parallel to the separation between the electrodes and is being attenuated—as is often the case where an external electrode is grounded or connected to the signal source—the two electrodes will see different levels of A. C. signal. Even small differences in electrode location can introduce large errors if there are significant changes in solution conductivity of dielectric constant from point to point: for instance, in systems which combine two different phases, such as a liquid and a gas or two immiscible liquids.

SUMMARY OF THE INVENTION

According to its major aspects and broadly stated, the present invention is a device for use in electrochemical measurements. The device comprises means for measuring a reference potential and producing a corresponding reference potential signal, means for measuring a redox potential and producing a corresponding redox potential signal, and means for coupling the reference potential and the redox potential signals. Both measuring means have active portions, and these portions are positioned to have a common geometric center.

More specifically, the present invention combines a mercury-calomel (or silver-silver chloride) reference electrode with an auxiliary platinum electrode in such a way that the two share a common geometric axis and thus are virtually immune to geometrically-induced measurement errors.

The reference electrode portion of the present invention may be of conventional design. The active portion of the platinum electrode, or redox electrode, however, forms a circle or "halo" around the porous tip of the reference electrode. This places the active portions of both electrode types adjacent to each other with a common geometric center and, therefore, effectively at the same point in the solution.

The "halo" may consist of a platinum wire held in position by an insulator, a platinum tube slipped around the reference electrode and sealed to its outer surface, or, preferably, a thin film of platinum fired directly onto the glass of the reference electrode: for example, by thermal decomposition of a paste or ink containing ammonium chloroplatinate or another easily-decomposed platinum compound. Such a layer will not add significantly to the electrode's diameter, and will function well so long as it is protected from abrasion and from chemical poisons such as sulfides.

The platinum layer preferably extends back along the outer surface of the reference electrode to the point of connection with external wiring, and thus fully encloses the high-impedance inner electrode and forms an electrostatic shield which helps to guard it from the effects of high-frequency signals other than the one at its tip. Alternatively, the platinum may form only a single conductive stripe along the electrode's length, or the connection and, optionally, shielding may be provided through some other type of conductor. Only the short end portion of the "halo" electrode, directly adjacent to the porous reference electrode tip, is exposed to the solution under study and needs to be of platinum; the remainder of the "halo" electrode is isolated electrically and chemically from the solution by, preferably, a TEFLON sleeve, fired-on glaze, or a similar nonconductive, chemically resistant material, and may be of any reasonably inert and electrically-conductive material.

One or more capacitors are connected between the reference electrode and the platinum "halo" to couple the low-impedance "halo" A.C. signal onto the higher-impedance reference electrode line. A selection of capacitance values is desirable since the optimum value is likely to vary depending on the application, the frequency, and the type of potentiostat to be used.

The capacitance may either be located remotely or may be made an integral part of the electrode assembly. Preferably, a small sealed module is mounted directly on the electrode cap, at the end opposite the porous plug, and contains a selection of capacitors capable of being used separately or in combination, by means of switching devices, to yield a wide range of capacitances in the range between one nanofarad and one microfarad. Monolithic ceramic "chip" capacitors are especially suitable for this purpose, since they provide large capacitance values in little space. The switching devices are preferably spash- and corrosion-proof; some newer dual-inline-packaged (DIP) switches and miniature rotary switches, for instance, are available off-the-shelf with built-in, synthetic rubber seals.

The geometry of the electrode is an important feature of the present invention. The electrode is preferably a standard, mercury-calomel reference electrode in the form of a tube with a thin platinum layer applied by thermal deposition to the sides of it, and with a chemically and electrically insulating layer on the platinum layer, except for a small portion on one end, so that the platinum redox electrode is coaxial with the reference electrode and the active portion of the reference electrode is adjacent to the active portion of the redox electrode. This arrangement makes the present electrode immune to geometrically-induced measurement errors, gives it superior high-frequency response and simplifies matching the electrode to the potentiostat.

Another feature of the present invention is the selection of capacitors for coupling the reference and the redox potentials. The capacitances can be selected, preferably by pressing switches or dialing the capacitance needed for the particular application. This feature gives the present invention considerable flexibility.

Other features and advantages of the present invention will be apparent to those skilled in the art from a careful reading of the Detailed Description of a Preferred Embodiment presented below and accompanied by the drawings.

DETAILED DESCRIPTION OF A PREFERRED EMBODIMENT

Figure 1:
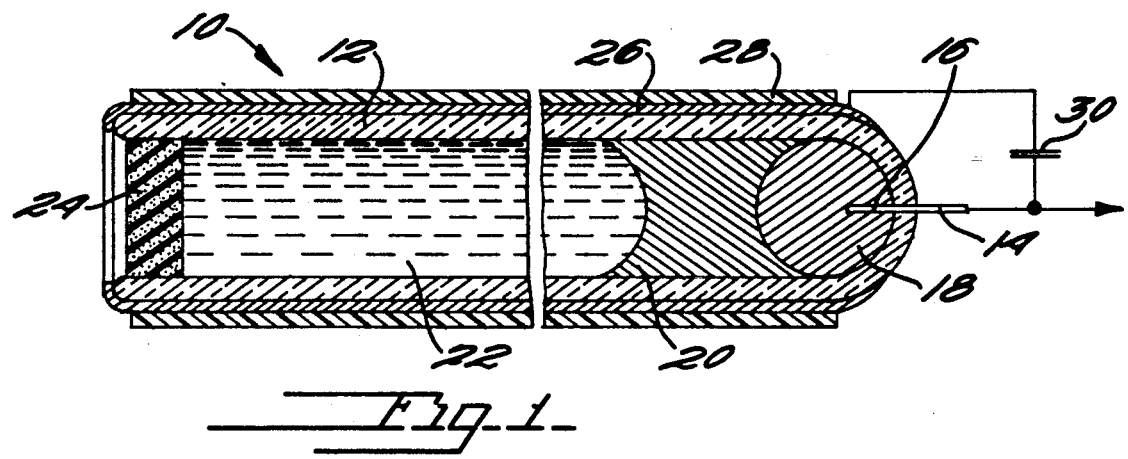
FIG. 1 is a side cross-sectional view of an electrode according to a preferred embodiment of the present invention.

A preferred embodiment of the invention consists of a high-frequency reference electrode 10 made from a tube 12 of borosilicate glass into one end of which is sealed a platinum wire 14. The inner end 16 of wire 14 is wetted by, and holds by surface tension, a small amount of mercury 18, around which is packed a paste 20 of calomel, or of mercury and calomel intimately mixed, wetted by saturated potassium-chloride solution 22 which also fills much of the remainder of tube 12. Tube 12 may be straight and of uniform cross-section, as shown, or may take any other form as may be required for a given application. Into the opposite end of tube 12 is sealed a porous plug 24 consisting, for example, of sintered glass frit.

Reference numerals 12 through 24, collectively, represent the elements of electrode 10 that make up a saturated calomel reference electrode such as may be purchased from a wide variety of laboratory equipment supplies, but deprived of its usually sealed end cap through which connection is made between wire 14 and external circuitry.

Deposited on, and completely covering the outer surface of tube 12, except for a short length immediately adjacent to wire 14, is a thin layer 26 of pure, metallic platinum. This may be formed, for example, by thinly coating the tube—after wire 14 is sealed in, but before filling in with other ingredients—with a paste of water and ammonium chloroplatinate. When the paste has dried, the tube is raised to a red heat, decomposing the salt to leave behind a coating of metallic platinum. Several proprietary compositions exist for this purpose and are widely used in the ornamental glass and ceramic trades.

Layer 26 is covered for most of its length, save for a ring-shaped area surrounding porous plug 24 and for the short length nearest wire 14, by a sheath 28 made from TEFLON heat-shrink tubing. Sheath 28 provides not only chemical and electrical isolation, but also some degree of protection against mechanical shock and abrasion. Layer 26 forms a redox electrode which produces a redox potential signal. The redox potential signal is coupled with the reference potential signal of the reference electrode by at least one capacitor 30 and the coupled signal forwarded to a potentiostat (not shown).

Figure 2:
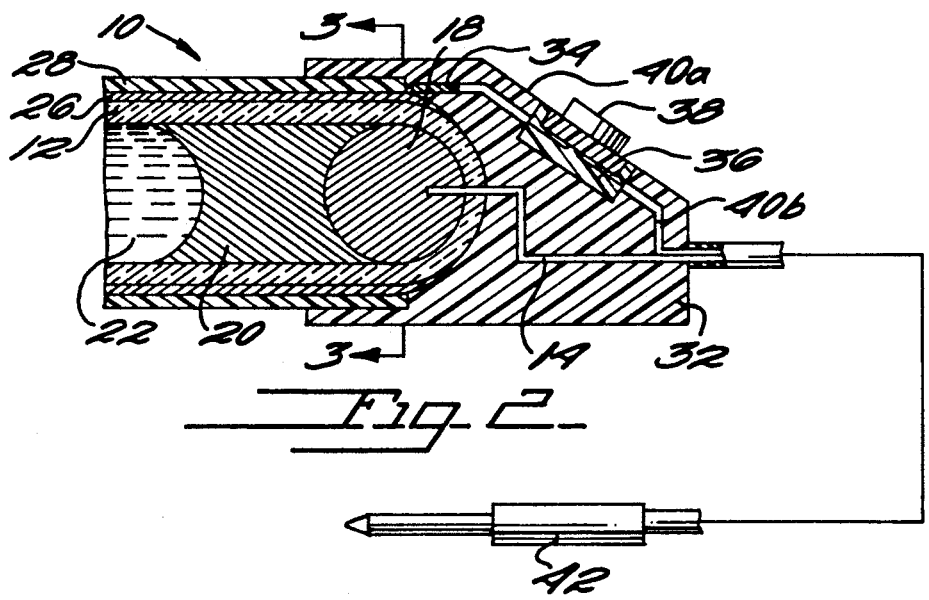
FIG. 2 is a partial, side cross-sectional view of an alternative embodiment of an electrode according to the present invention showing in particular an embodiment with capacitors incorporated.

FIG. 2 shows a partial side cross sectional view of electrode 10 but with an end fitting 32 for holding at least one capacitor 34 in contact with platinum layer 26 and at least one switch 36 to select capacitor 34. End fitting 32 is preferably a solid molded block of epoxy resin or similar material, which also encloses the end of tube 12, adjacent wire 14 and covers the portion of platinum layer 26, adjacent to wire 14, that is not covered by sheath 28. Switch 36 is operated by a pushbutton, knob or other mechanical actuating device 38. Wires 40a and 40b connect capacitor 34 to switch 36 and switch 36 to wire 14. The coupled output signal of the redox electrode, platinum layer 26, and the reference electrode, the output of which is carried in wire 14, is run to a potentiostat (not shown in FIG. 2) via a flexible, thickly-insulated wire terminating in a pin tip connector 42 that is compatible with most standard laboratory potentiostats.

Figure 3:
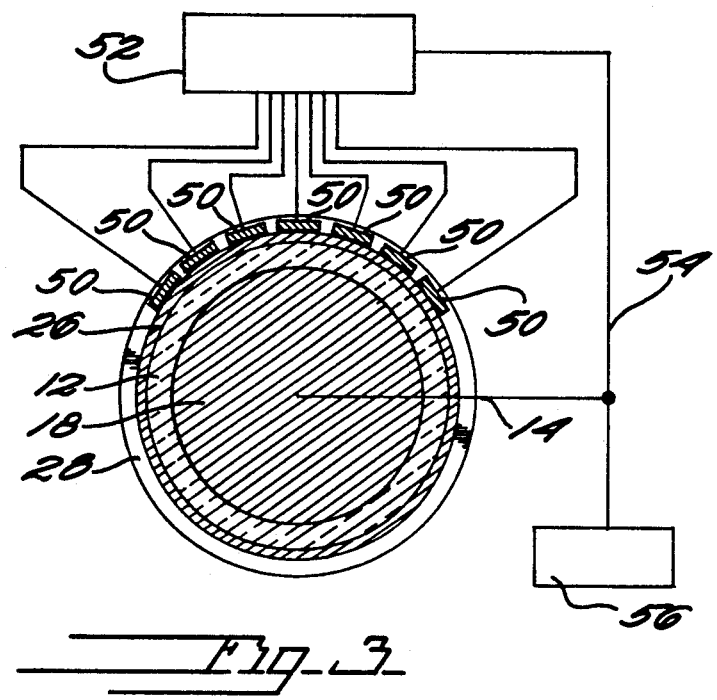
FIG. 3 is an end cross sectional view to show the connection of the capacitors to the electrode.

As best seen in FIG. 3, which is a cross sectional view along lines 3—3 of FIG. 2, the exposed portion of layer 26, adjacent to wire 14, is preferably connected to a plurality of monolithic ceramic "chip" capacitors 50. Depending on the thickness of layer 26, these capacitors may be bonded or soldered directly to it, or may be similarly fastened to a thickened area of metal laid down on top of it by hybrid-circuit techniques: for instance, an area printed with silver-loaded ink and subsequently fired. Depending on the number and size of these capacitors, they may be spaced equally around the circumference of glass tube 12 or may be clustered at one side as shown.

The opposite terminals of capacitors 50 are connected to a miniature, multipole switching device 52 which is sealed against moisture and contamination, and corresponding to switch 36 in FIG. 2.

A likely candidate for switching device 52 is the Omron A6D sealed DIP switch, which is available in two-, four-, six-, eight-, and ten switch versions and in a variety of actuator styles; the A6D-8100 eight-switch, top-actuated style with raised actuators is preferred. One capacitor 50 is connected to each section of switching device 52. The opposite terminals of all switch sections are connected to a common bus 54, to which wire 14 is also connected and continued to potentiostat 56. Alternatively, a rotary switch of similar construction (such as one of the Omron A6C series) could be used, with bus 54 corresponding to the "common" terminal.

Capacitors 50 have various values of capacitance so that one or more may be selected, using device 52, to give a total capacitance matched to the input circuit of the potentiostat. For example, in the arrangement shown, the capacitors might have values starting with 0.001 microfarad and increasing successively by powers of two, allowing values from 0.001 to 0.255 microfarads to be selected through simple binary switch settings. More realistically, since matching permits a rather broad selection of values, a quasi-binary sequence of common stock values (such as 0.001, 0.0022, 0.0047, 0.01, 0.022, 0.047, 0.1 and 0.22 microfarads) could be used to provide much the same effect without requiring custom capacitors. A similar approach could be used with capacitors selected by a rotary switch.

Figure 4:
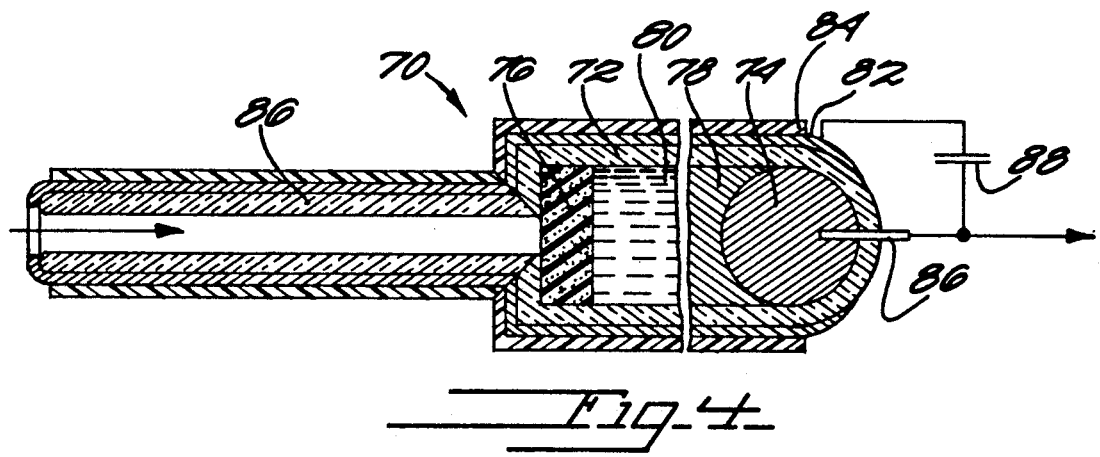
FIG. 4 is a partial, side cross-sectional view of another embodiment of an electrode according to the present invention.

FIG. 4 shows a modified embodiment of the present electrode generally indicated by the reference character 70 comprising a borosilicate glass tube 72 housing a small quantity of mercury 74 at one end and a porous end plug 76 at the other with calomel 78 adjacent to mercury 74 and potassium chloride solution 80 adjacent to end plug 76. As before, tube 72 is surrounded with a layer of platinum 82 which is in turn surrounded with a layer 84 of a chemically and electrically inert material such as TEFLON. Attached to the end of glass tube 72 is a capillary tube 86 which carries platinum layer 82 and TEFLON layer 84 to its tip. A wire 86 is embedded in mercury 74 and carries the output of the reference electrode part of electrode 70. The output of the platinum, redox electrode is coupled to wire 86 by at least one capacitor 88.

By using glass capillary tubing to make the reference electrode, or by attaching a long capillary tube to the end of a larger-scale reference electrode, and then by plating the exterior of this tube with platinum and covering it with an insulating sheath, it is possible to make a electrode of very small dimensions which still would function well at high frequencies. Such an electrode would be useful, for instance, in studying the electrochemical environment within a corrosion pit or a stress-corrosion crack through high-frequency techniques.

It will be apparent to those skilled in the art that many changes and substitutions can be made to the preferred embodiment herein described without departing from the spirit and scope of the present invention which is defined by the appended claims.

What is claimed is:

1. A device for use in electrochemical measurements of a fluid, comprising:
   first measuring means for measuring a reference potential and producing a reference potential signal, said first measuring means having a first active portion and a first axis;
   second measuring means carried by said first measuring means for producing a redox potential signal, said second measuring means having a second active portion and a second axis, said second measuring means carried by said first measuring means so that said first and second axes are coaxial, said first and said second active portions having a common geometric axis, said first and second active portions adapted to contact with said fluid when said device is placed in said fluid; and
   means for capacitively coupling said reference potential signal to said redox potential signal.

2. The device as recited in claim 1, wherein said first measuring means further comprises a tube having a surface and an end, said first active portion being disposed at said end, and wherein said second measuring means is carried by said surface so that said second active portion is concentric to said first active portion at said end.

3. The device as recited in claim 1, wherein said first measuring means has a surface and said second measuring means further comprises a layer of platinum carried by said surface.

4. The device as recited in claim 1, wherein said coupling means further comprises:
   at least one capacitor connected between said first active portion and said second active portion, said capacitor having a capacitance; and
   means for varying said capacitance.

5. The device as recited in claim 1, wherein said first measuring means is selected from the group consisting of a mercury-calomel reference electrode and a silver-silver chloride reference electrode.

6. A device for use in electrochemical measurements of a fluid, comprising:
   a reference electrode for producing a reference potential signal, said reference electrode having an outer surface and an active portion, said active portion having a first axis and adapted to contact said fluid;
   a first layer of electrically conducting material carried by said outer surface of said reference electrode, said first layer for producing a redox potential signal, said first layer covering a first part of said outer surface leaving said active portion exposed, said first layer being spaced apart from said active portion and having a second axis, said first layer carried by said reference electrode so that said first axis and said second axis are coaxial;

a second layer of electrically and chemically insulating material carried by said first layer, said second layer leaving exposed a part of said first layer adjacent to said active portion of said reference electrode, said part of said first layer adapted to contact said fluid when said device is placed in said fluid; and means for capacitively coupling said redox potential signal to said reference potential signal, said coupling means including:

a plurality of capacitors, and means for electrically connecting one or more of said plurality of capacitors between said first layer and said active portion of said reference electrode whereby said redox potential signal and said reference potential signal are electrically coupled.

7. The device as recited in claim 6, wherein said first layer is platinum.

8. The device as recited in claim 6, wherein said first layer is applied to said reference electrode by thermal decomposition of chloroplatinate.

9. The device as recited in claim 6, wherein said reference electrode further comprises a glass tube having a closed end and an open end, and wherein said active portion is at said open end.

10. The device as recited in claim 6, wherein said reference electrode further comprises a glass tube having a closed end and an open end, said tube having a porous plug at said open end and mercury inside said tube near said closed end, an electrically conducting wire having one end in said mercury and an opposing end extending through said closed end, said tube having potassium chloride near said open end adjacent said porous plug and mercuric chloride between said mercury and said potassium chloride.

11. The device as recited in claim 6, wherein said reference electrode has a closed end and an open end, and wherein said coupling means is carried by said closed end.

12. The device as recited in claim 6, wherein said plurality of capacitors further comprises a plurality of ceramic capacitors, and wherein said connecting means further comprises at least one dual in-line package switch, said switch in operative connection with said capacitors.

* * * * *